(12) United States Patent
Fayez et al.

(10) Patent No.: US 11,320,414 B2
(45) Date of Patent: May 3, 2022

(54) METHOD FOR DIFFERENTIATING BETWEEN NATURAL FORMATION HYDROCARBON AND CRACKED HYDROCARBON USING MUD GAS MEASUREMENTS

(71) Applicant: SAUDI ARABIAN OIL COMPANY, Dhahran (SA)

(72) Inventors: Fahad A. Fayez, Dammam (SA); Ali S. Alsaad, Dammam (SA); Ibrahim M. Meer, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 97 days.

(21) Appl. No.: 16/941,115

(22) Filed: Jul. 28, 2020

(65) Prior Publication Data

US 2022/0034862 A1 Feb. 3, 2022

(51) Int. Cl.
*G01N 33/28* (2006.01)
*E21B 49/08* (2006.01)
*G01N 33/00* (2006.01)

(52) U.S. Cl.
CPC ....... *G01N 33/2823* (2013.01); *E21B 49/081* (2013.01); *E21B 49/086* (2013.01); *G01N 33/0067* (2013.01)

(58) Field of Classification Search
CPC ............ G01N 33/0067; G01N 33/2823; E21B 49/081; E21B 49/086
See application file for complete search history.

(56) References Cited

U.S. PATENT DOCUMENTS

| | | | |
|---|---|---|---|
| 4,457,374 A | 7/1984 | Hoekstra et al. | |
| 9,671,381 B2* | 6/2017 | Karoum | G01N 1/2294 |
| 10,167,676 B2* | 1/2019 | Calleri | G01N 33/0036 |
| 2010/0089120 A1 | 4/2010 | Hanson | |
| 2010/0126727 A1 | 5/2010 | Vinegar et al. | |
| 2013/0233057 A1* | 9/2013 | Karoum | G01N 33/2823 73/31.07 |
| 2013/0263647 A1 | 10/2013 | Barrett et al. | |
| 2016/0102510 A1* | 4/2016 | Mitchell | G01N 21/274 175/24 |

(Continued)

OTHER PUBLICATIONS

Donovan, "What Causes Mudlogging Mud Gas Response Vary?" American Association of Drilling Engineers, AADE-19-NTCE-050 (Year: 2019).*

(Continued)

*Primary Examiner* — John Fitzgerald
(74) *Attorney, Agent, or Firm* — Osha Bergman Watanabe & Burton LLP (57) ABSTRACT

A method may include collecting a sample of mud gas during a wellbore drilling operation, associating the sample with a depth of the wellbore, and detecting concentrations of methane, ethane and ethylene. With the detected concentrations, a determination can be made as to the degree of a mud gas artifact event occurring, including determining the differences between the logarithmic values of concentrations of methane and total C2 concentration and the logarithmic values of total C2 concentration and ethane. A visually displayed mud gas log is modified to indicate the degree of the determined mud gas artifact event.

15 Claims, 4 Drawing Sheets

(56) References Cited

U.S. PATENT DOCUMENTS

| | | | |
|---|---|---|---|
| 2016/0153955 A1* | 6/2016 | Strapoc | E21B 47/10 175/40 |
| 2016/0273355 A1 | 9/2016 | Gosney et al. | |
| 2016/0319662 A1 | 11/2016 | Zuo et al. | |
| 2017/0254155 A1 | 9/2017 | Calleri | |
| 2018/0195383 A1* | 7/2018 | Smith | G01N 1/4022 |
| 2018/0245465 A1 | 8/2018 | Khan et al. | |

OTHER PUBLICATIONS

Hammerschmidt et al. "Real-time drilling mud gas monitoring for qualitative evaluation of hydrocarbon gas composition during deep sea drilling in the Nankai Trough Kumano Basin," Geochemical Transactions (Year: 2014).*

Qubaisi Khalid et al: "Using Drill Bit Metamorphism to Aid in Formation Evaluation of Tight Gas Reservoirs", International Petroleum Technology Conference, [Online] Jan. 13, 2020, XP055793235 pp. 1-9, (9 pages).

International Search Report and Written Opinion issued in Application No. PCT/US2020/046414, dated Apr. 15, 2021 (14 pages).

Regan M. et al: "Near Real-Time Monitoring of PDC Bit Condition and Associated NPT Mitigation Using Online Alkene Detection", IADC/SPE Asia Pacific Drilling Technology Conference and Exhibition, Aug. 27, 2018, XP055793325, DOI: 10.2118/190997-MS, pp. 1-11, (11 pages).

Wenger L M et al: Drill-bit metamorphism: Recognition and impact on show evaluation:, SPE Annual Technical Conference and Exhibition 2009 (ATCE 2009): New Orleans, Louisiana, USA, Oct. 4-7, 2009, Red Hook, NY: Curan, US, No. SPE 125218, Oct. 4, 2009, pp. 4565-4573, XP008130466, DOI: 10.2118/125218-MS, (9 pages).

Ighodalo Endurance et al: "Increasing Certainty in Formation Evaluation Utilizing Advanced Mud Logging Gas Analysis", SPE Kingdom of Saudi Arabia Annual Technical Symposium and Exhibition, Apr. 24, 2017, SP055793318, DOI: 10.2118/188039-MS, pp. 1-18 (18 pages).

Wenger, Lloyd M. et al., "Drill-Bit Metamorphism: Recognition and Impact on Show Evaluation", SPE 125218, Society of Petroleum Engineers, Oct. 2009 (9 pages).

Ighodalo, Endurance et al., "Increasing Certainty in Formation Evaluation Utilizing Advanced Mud Logging Gas Analysis", SPE-188039-MS, Society of Petroleum Engieers, Apr. 2017 (18 pages).

Carcione, Ettore et al., "Alkenes Detection From Drill Bit Metamorphism and Real-Time Geochemical Elemental Analysis on Drill Cuttings Aids Drilling Optimization and Geo-Steering in Tight Unconventional Laterals", URTeC: 2697162, Unconventional Resources Technology Conference, Jul. 2017 (6 pages).

Faber, Eckhard et al., "Gaseous hydrocarbons of unknown origin found while drilling", Advances in Organic Geochemistry, Pergamon Press plc, vol. 13, Nos. 4-6, 1988, pp. 875-879 (5 pages).

Ferroni, Gionata et al., "Improved Formation Evaluation While Drilling with a New Heavy Gas Detector", SPWLA 53rd Annual Logging Symposium, Jun. 2012 (12 pages).

\* cited by examiner

METHOD FOR DIFFERENTIATING BETWEEN NATURAL FORMATION HYDROCARBON AND CRACKED HYDROCARBON USING MUD GAS MEASUREMENTS

BACKGROUND

In petroleum geology and chemistry, cracking is the process whereby complex organic molecules, such as kerogens or long-chain hydrocarbons, are broken down into simpler molecules, such as light or short-chain hydrocarbons, by the breaking of carbon-carbon bonds. The petroleum industry uses a similar yet artificial version of the cracking process with a combination of heat and catalysts. Cracking of long-chain hydrocarbons yields saturated hydrocarbons, such as methane, ethane, propane, and unsaturated hydrocarbons, such as ethylene and propylene. The rate of cracking and the end products are strongly dependent on the temperature.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed relate to a method of determining a degree of artifact gases and displaying such determination. Such a method may comprise collecting a sample of mud gas from a drilling fluid used during a drilling operation to form a wellbore, associating the collected mud gas sample with a depth of the wellbore during the drilling operation, and detecting the concentration of ethane, the concentration of ethylene, and the concentration of methane in the drilling fluid at the depth. The method may also comprise determining the concentration of total C2 gases in the drilling fluid at the depth. The method may also include determining a first difference between the logarithmic value of the detected concentration of methane and the logarithmic value of the determined concentration of total C2 gases at the depth, and determining a second difference between the logarithmic value of the determined concentration of total C2 gases and the logarithmic value of the detected concentration of ethane at the depth. The method may comprise determining the degree of artifact gases present in the drilling fluid at the depth based upon the detected concentration of methane and ethylene, and the determined concentration of total C2 gases, the first difference and the second difference. Modifying a visually displayed mud drilling log to reflect the determined degree of artifact gases present in the drilling fluid at the depth may also be part of the method.

The method in some embodiments may include determining whether the detected value of the concentration of ethylene in the mud gas is greater than 0. In some embodiments, the method may include determining whether the determined value of the concentration of total C2 gases is greater than the detected value of the concentration of methane in the mud gas. In some embodiments, determining whether a first difference is greater than a second difference may be part of the method. In The method of claim 1 where determining the degree of artifact gases present in the drilling fluid at the depth includes determining whether a first difference is equal to or less than a second difference at the depth.

The method may further include in some embodiments that an alert is displayed on a visual display associated with the determined degree of artifact gases present in the drilling fluid at the depth.

The method may include visually displaying a first detected concentration trace, a second detected concentration trace, and a determined concentration trace on the mud gas log for a given depth interval. In some embodiments, the first detected concentration trace is the concentration of methane, the second detected concentration trace is the concentration of ethane, and the determined concentration trace is the concentration of total C2 gases. In some other embodiments, the area between the first detected concentration trace and the determined concentration trace is indicated by a first color or pattern. In other embodiments, the area between the determined concentration trace and the second detected concentration trace is indicated by a second color or pattern.

The method may further include modifying the rate of penetration (ROP) used in the drilling operation in response to the determined degree of artifact gases present in the drilling fluid at the depth. In some embodiments, the ROP is increased in response to the determined degree of artifact gases. In some other embodiments, the ROP is decreased by a fixed percentage of the ROP used in the drilling operation. In some embodiments, the method may further include modifying the rotation per minute (RPM) of the drill bit or the drill string, as applicable, used in the drilling operation in response to the determined degree of artifact gases present in the drilling fluid at the depth. The method may include modifying the weight-on-bit (WOB) used in the drilling operation in response to the determined degree of artifact gases present in the drilling fluid at the depth in some embodiments.

Other aspects and advantages of this disclosure will be apparent from the following description made with reference to the accompanying drawings and the appended claims.

BRIEF DESCRIPTION OF DRAWINGS

Certain embodiments of the disclosure will be described with reference to the accompanying drawings, where like reference numerals denote like elements. It should be understood, however, that the accompanying figures illustrate the various implementations described and are not meant to limit the scope of various technologies described.

In the figures, down are toward or at the bottom and up are toward or at the top of the figure. "Up" and "down" are generally oriented relative to a local vertical direction. However, as used throughout this disclosure, the terms "uphole" and "downhole" may refer to a position within a wellbore relative to the surface, with "uphole" indicating direction or position closer to the surface entry point and "downhole" referring to direction or position farther away from the surface entry point. One of ordinary skill in the art understands that an object or a process may be "uphole" or "downhole" of another object or process while having the same true vertical depth relative to the surface of the earth.

DETAILED DESCRIPTION

Confirming the presence of hydrocarbons in the target reservoir is an important aspect of exploration drilling. Mud gas acquisition and analysis is a tool used in detecting indigenous hydrocarbons in a hydrocarbon-bearing formation. Monitoring of mud gases is done during the creation of the wellbore and penetration of the reservoir to detect and confirm the presence of hydrocarbons. As well, monitoring mud gases is used as a measurement of safe operations. The presence of a strong amount of hydrocarbons indicates that the mud weight may be insufficient to properly contain the pressures in the downhole formations, and that modification to the properties of the mud may be required before proceeding.

Gas artifacts include the occurrence of unsaturated gas components ethylene, propylene and butylene compounds during drilling operations. Olefins are not "geologically stable", that is, they do not last very long in the environment before reacting to another compound. Olefins do not occur naturally in the Earth except in very shallow environments where biological activity is present.

During the drilling operation, mechanical energy is applied to the bit through the drill string or the drilling fluid. The mechanical energy will be mostly transformed by the drill bit into work (that is, rate of penetration or ROP). This work is partly transformed and dispersed by the bit friction against the rock into heat. The intense heat generated by drill bit "fatigue" during drilling, in conjunction with the composition of the drilling fluid (especially fluids with hydrocarbons) and hydrocarbons and non-hydrocarbon gases present in the formation being drilled, has been recognized to generate these gas artifacts. As previously stated, the gas artifacts are not naturally present; they are manufactured olefins—"cracked" hydrocarbons—formed at the drill bit during drilling operations. Their detection may indicate that drilling behaviors, such as the rate of penetration (ROP), the weight on bit (WOB), the revolutions per minute (RPM) of the bit or the drill string, or other parameters, may be inappropriate for the situation in which the operator finds him or herself.

In addition, the detection of hydrocarbon gases is also essential for post-drilling analysis of the intervening formations and reservoir by geologists and reservoir engineers. The alteration of natural formation gases and even oil-based drilling fluid into non-naturally-occurring gas artifacts (that is, alkenes) can affect the compositional analysis of the target formation and, in severe cases, give a "false positive" regarding the presence or make-up of indigenous hydrocarbons in a given formation. Identifying when cracking has occurred is important when more studious, post-drilling activities occur. Not recognizing when cracking has occurred may negatively affect the determination of the potential value of the hydrocarbon-bearing formation. As well, failure to see the cracking effect may also affect decisions on how best to initiate production, manage the processing of the reservoir through equipment selection, and incorrectly estimate fluid production rates.

Drilling with oil-based drilling fluids in certain circumstances can produce thermal cracking at the drill bit. This effect, called drill bit metamorphism (DBM), introduces gas artifacts into the drilling fluid or "mud" that are produced by the interaction between the drill bit, rocks and the drilling fluid. Thermally cracked hydrocarbons—alkenes or olefins, such as ethylene and propylene—originate at the drill bit due to the heat of friction of the drill bit against the formation material. The hot, non-oxygenated metallic surface of the drill bit, the heated non-metallic surface of the formation material, and the instantaneous heat of friction between the two, may create an environment that vaporizes and catalyzes not only light hydrocarbons in the formation matrix, which breaks apart under the heat and weight of the drill bit, but also some hydrocarbons that make up the drilling fluid into cracking into hydrogen and alkenes. After quenching in the bulk drilling fluid, the cracked hydrocarbons circulate back to the surface and are detected in the mud logging system.

A method and system for determining the presence and severity of hydrocarbon cracking while drilling and differentiating between natural formation hydrocarbons and artificially-generated hydrocarbons is presented. The method and system provide for the monitoring and memorialization of detection of olefin products. Active feedback for an operator will assist the him or her in real time to adjust drilling behaviors to mitigate such occurrences. As well, memorialization and notes on the mud gas log helps geologists and reservoir engineers to adjust their potential findings based on the data for such artifacts.

Figure 1:
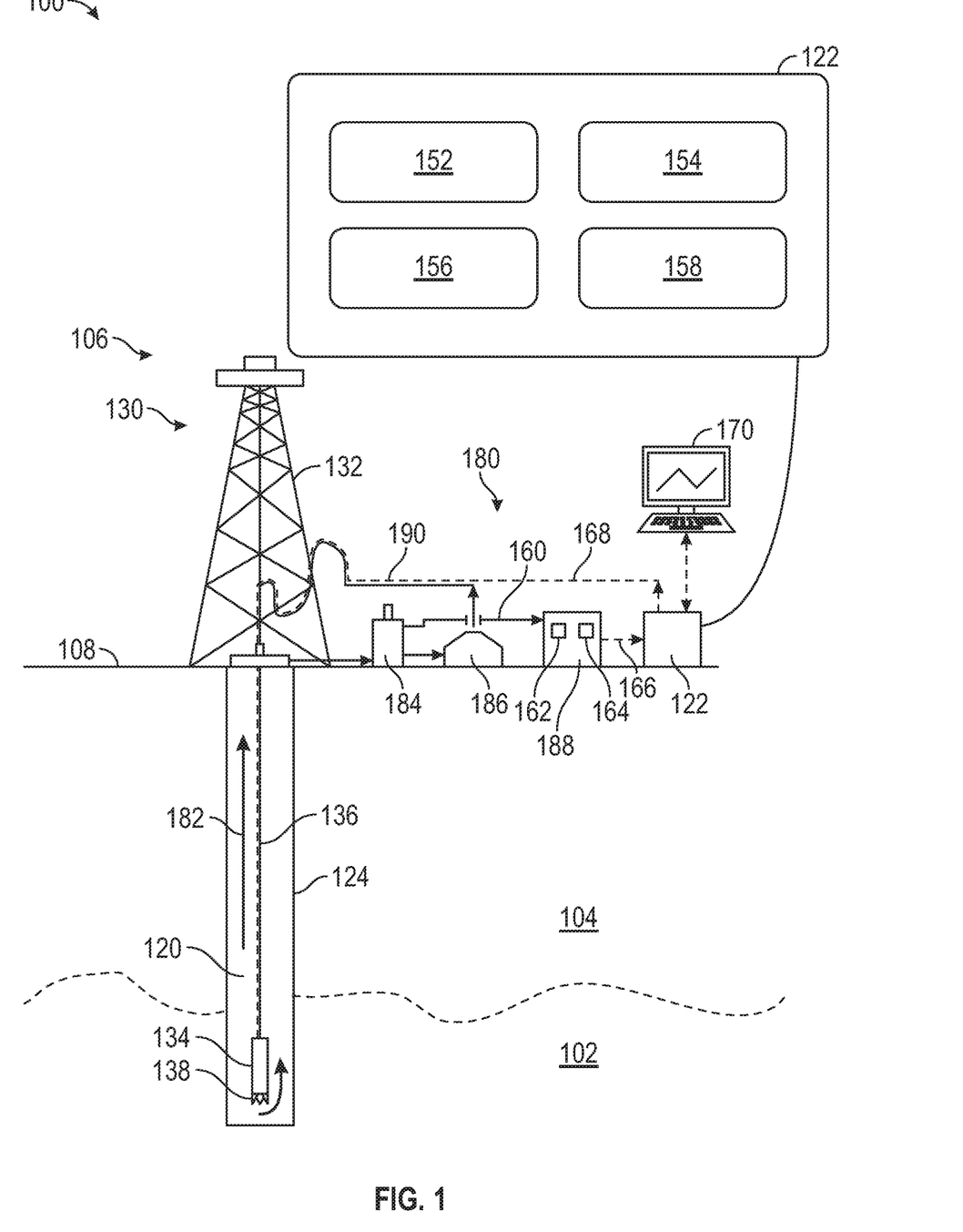
FIG. 1 is a diagram that illustrates a well environment in accordance with one or more embodiments.

FIG. 1 is a diagram that illustrates a well environment in accordance with one or more embodiments. In the illustrated embodiment, the well environment 100 includes a hydrocarbon-bearing formation 102 located in a subsurface formation ("formation") 104 and a well system 106.

The formation 104 may include a porous or fractured rock formation that resides underground, beneath the surface 108 of the Earth. The surface 108 may be dry land or ocean bottom. The well system 106 may be for a hydrocarbon well, such as an oil well, a gas well, a gas condensate well, or a mixture of hydrocarbon-bearing fluids. The hydrocarbon-bearing formation 102 may be a hydrocarbon reservoir defined by a portion of the formation 104 that contains (or that is at least determined to or expected to contain) a subsurface pool of hydrocarbons, such as oil and gas. The formation 104 and the hydrocarbon-bearing formation 102 may each include different layers of rock having varying characteristics, such as degree of density, permeability, porosity, and fluid saturations. In the case of the well system 106 being operated as a production well, the well system 106 may facilitate the extraction of hydrocarbons (or "production") from the hydrocarbon-bearing formation 102. In the case of the well system 106 being operated as an injection well, the well system 106 may facilitate the injection of substances, such as a gas or water, into the hydrocarbon-bearing formation 102. In the case of the well system 106 being operated as a monitoring well, the well system 106 may facilitate the monitoring of various characteristics of the formation 104 or the hydrocarbon-bearing formation 102, such as reservoir pressure or saturation.

The well system 106 may include a wellbore 120, a well control system (or "control system") 122 and a drilling system 130. The control system 122 may regulate various operations of the well system 106, such as well drilling operations, well completion operations, well production operations or well or formation monitoring operations. In some embodiments, the control system 122 includes a computer system that is the same as or similar to that of computer system 1000 described with regard to at least FIG. 4.

The wellbore 120 may include a bored hole that extends from the surface 108 into a target zone of the formation 104, such as the hydrocarbon-bearing formation 102. Wellbore 120 is defined by wellbore wall 124. Although shown as a vertical well, wellbore 120 may take a deviated or horizontal configuration, the embodiment methods and systems are adaptable and applicable to all wellbore configuration types.

The wellbore 120 may provide for the circulation of drilling fluids or drilling "mud" 182 during drilling operations using a mud circulation system 180. Drilling mud 182 flows downhole through the drill string 134, out the drill bit 138 (cooling the drill bit 138 at the same time from heat of friction against the face of the wellbore 120, and back uphole through the annulus formed by the drill pipe 136 and the wellbore wall 124, carrying cuttings and other debris from the bottom of the wellbore 120.

In embodiments of the method, mud gas samples are collected from the drilling fluid used during a drilling operation. Upon reaching the surface 108, the drilling mud 182 passes into mud receiving tank 184, where the cuttings are separated from the drilling mud 182. I addition, in the mud receiving tank 184 the drilling mud 182 is agitated such that it releases any dissolved gases in the drilling mud 182, including artifact gases. These mud gases are passed through to the mud logging system 188 via the gas sample line 160. The now-degassed drilling mud 182 is passed to the mud storage tank 186, where it is held until it is pumped back to the drill string 134 via the mud return line 190 and then back downhole to repeat the drilling mud circulation cycle.

The mud circulation system 180 may provide useful operational information for operation and control of drilling activities. In some embodiments, the mud gases are portioned and run through a series of analyzers, for example, a total hydrocarbon analyzer 162 and a high-resolution gas chromatograph 164, in the mud logging system 188. Such analysis helps determine the volume and concentrations of possible formation gases, if present, in the drilling mud 182. A spike in flammable gas detection that has light petroleum gas (LPGs) components (that is, propane, butanes) may indicate penetration of a hydrocarbon-bearing formation that has a formation pressure that is greater than the current mud weight. As previously described, the detection of artifacts may indicate operational issues of the drill bit 138 and its interaction with a formation, such as subsurface formation 102 or hydrocarbon-bearing formation 104. Each requires immediate attention and action to mitigate the condition.

In embodiments, the concentration of ethane, ethylene (an artifact gas), and methane in the drilling fluid are detected by the mud logging system 188. As previously stated, one or more analyzers are used to detect the eluted mud gases. In some other embodiments, other wellbore gases are detected, including but not limited to, propane, normal butane, isobutane, normal pentane, normal hexane, propylene, butylenes, and combinations thereof.

In some embodiments, the mud logging system 188 is also configured to provide mud gas data 158 to well control system 122 through mud logging signal line 166. Such mud gas data 158 may include, but is not limited to, the detected concentration of methane (C1), the detected concentration of ethane (C2), and the detected concentration of ethylene (C2=).

In some embodiments of the systems and method, the well control system 122 is configured to determine one or more cumulative concentration values. For example, well control system 122 may determine a cumulative total C2 gas concentration (C2T) by the summation of a given detected concentration of ethane and a given detected concentration of ethylene. Well control system 122 may then correlate these determined concentration values with their corresponding detected concentration values into the mud gas data 158. As well, the well control system 122 may correlate the detected and determined concentration values with the indicated depth of the drill bit and include that with the mud gas data 158.

In some embodiments, the depths associated with the detected and determined values of the mud gas concentrations (and thus the depths displayed on the mud gas log 156) are correlated based on depths reported at the drill site. As the mud gas is extracted from the drilling mud and is detected and values are determined, the depth, often referred to as "driller" depths, is recorded with these values.

The well control system 122 in some embodiments is configured to relay information, such as mud gas data 158 or a mud gas log 156, to a control terminal 170 for viewing by an external viewer. The information may be numerically or graphically displayed, or both. An external viewer may include a computer monitor, a television, a printer, or any other form of temporal or permanent version of record keeping and displaying that can be visually appreciated.

In some additional embodiments, the well control system 122 may utilize some or all of the mud gas data 158, in addition to a set of pre-determined instructions and algorithms retained in the memory of a computer system, to maintain or modify operations of drilling system 130 based upon the detected, determined, or a combination of both, values, as will be described later. Such maintenance or modifying operations as determined may be transmitted downhole from well control system 122 via control signal line 168.

The mud gas data 158 is detected, determined, or both, at the surface, so there is a "lag" in the data versus depth. The lag in data to depth may be in a range of from about 10 minutes to upwards of an hour depending on a variety of drilling and wellbore conditions and factors. In some embodiments, the wellbore control system 188 or human intervention may adjust the correlation of wellbore depth with the mud gas data 158 using such other variables as the mud flow rate uphole, the lag time between mud return and mud gas analysis, and the drill bit 138 penetration rate, to account for the estimated depth of the wellbore when the mud gas was created at the drill bit 138 to form a more "correct" mud gas log 156.

The wellbore 120 may be created, for example, by the drilling system 130 boring through the formation 104. In some embodiments, the drilling system 130 includes a drilling rig 132 and a drill string 134. The drill string 134 may include a drill pipe 136 and a drill bit 138. In some embodiments, the drill bit 138 includes a cutting drill bit having rotating teeth that can bore through the formation 104 to create the wellbore 120.

Supporting equipment for embodiments of the system may include additional standard components or equipment that enables and makes operable the described apparatuses, processes, methods, systems, and compositions of matter. Examples of such standard equipment known to one of ordinary skill in the art includes but are not limited to heat exchanges, pumps, blowers, single and multi-stage compressors, separation equipment, valves, switches, controllers and pressure-, temperature-, level- and flow-sensing devices.

Drilling or completion operations for the well system 106 may include a well logging operation to generate a well log 152 for the well system 106. A well log 152 for the well system 106 may include a record identifying characteristics of the wellbore 120 of the well system 106 (or the formation 104 surrounding the wellbore 120) versus a depth along the length of the wellbore 120, determined based on mud log data 154 obtained by way of a logging of the well system 106. A well log 152 may include, for example, an acoustic log, a sonic log, a resistivity log, borehole image log, a porosity log, a permeability log, or a nuclear magnetic resonance (NMR) log. Well logging of the well system 106 may include lowering a well logging tool into the wellbore 120 and operating the logging tool to detect characteristics of the wellbore 120 using sensors as the logging tool traverses the length or a portion thereof of the wellbore 120. The measurements or determined characteristics may be recorded in a corresponding well log 152 that provides a mapping of the detected values, or determined values (if the detected values are further processed mathematically), or both, versus depth in the wellbore 120. For example, a well log 152 for the well system 106 may include a mapping of the acoustic travel time (a detected value) or an associated porosity (a determined value from acoustic travel time) versus depth in the wellbore 120.

In some embodiments, and similar to the example previously given, a mud gas log 156 for the well system 106 may include a record identifying volume and composition properties of the drilling mud 182, and specifically the drilling mud 182 at a given time, which, in turn, relates to a depth along the length of the wellbore 120. In some embodiments, the well control system 188 creates a mud gas log 156, which is a record of mud gas data 158, including detected concentration values, determined concentration values, versus depth values, on an ongoing basis. The mud gas log 156 may include, but is not limited to, detected concentration of methane (C1), the detected concentration of ethane (C2), detected concentration of propane (C3), detected concentration of normal butane (C4n), detected concentration of iso butane (C4i), detected concentration of normal pentane (C5n), detected concentration of iso pentane (C5i), detected concentration of ethylene (C2=), detected concentration of propylene (C3=), determined concentration of total C2 gas (C2T), determined concentration of total C3 gas (C3T), and combinations thereof. The mud gas log 156 provides a mapping of the detected values, determined values, or both, versus depth in the wellbore 120.

In some embodiments, a first detected concentration trace, a second detected concentration trace, and a determined concentration trace are displayed visually on a mud gas log for a given depth interval. A trace is a line formed on a graph or plot where a set of concentration values (on a first axis) are correlated and plotted visually with the depth values (on a second axis) in which the concentration was detected or determined. In some embodiments, a detected trace comprises a set of detected concentration values of methane (C1) correlated with a set of depths at which the concentration values were detected. In some such embodiments, a detected trace is associated with a set of detected concentration values of ethane (C2) correlated with a set of depths at which the concentration values were detected. In some such embodiments, the determined trace is associated with a set of determined concentration values of total C2 gas (C2T) correlated with a set of depths at which the concentration values were determined.

Figure 2:
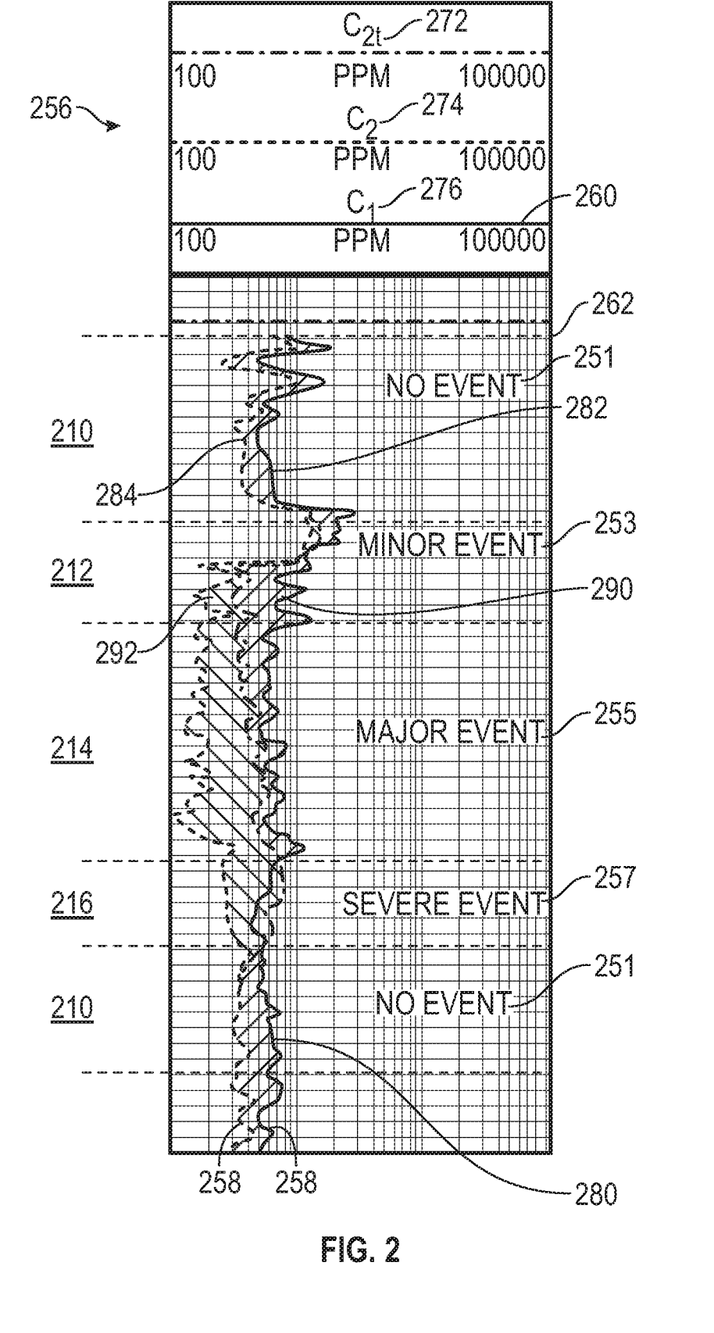
FIG. 2 is a representation of a mud gas log plotting detected and determined mud gas composition values versus depth for a drilling interval that has been graphically enhanced in accordance with one or more embodiments.

FIG. 2 is a representation of a mud gas log plotting detected and determined mud gas composition values versus depth for a drilling interval that has been graphically enhanced in accordance with one or more embodiments. In the illustrated embodiment, the mud gas log 256 includes plotted mud gas data 258 that forms traces of values of detected and determined concentrations of gases emanating from the circulating drilling mud versus the depth for a drilled interval of the wellbore in which such values were detected or determined. The mud gas log 256 displays and memorializes changing values for detected concentration of methane (C1) 276, the detected concentration of ethane (C2) 274, and the determined concentration of total C2 gas (C2T) 272, as traces 280 versus a drilling depth for an interval for the drilling of a wellbore. The traces 280 are shown for detected concentration of methane 276 (methane trace 282), detected concentration of ethane 274 (ethane trace 284), and determined concentration of total C2 gas (C2T trace 286).

In some other embodiments, other detected and determined concentration values are plotted on mud gas log 256. Traces may be provided for any detected or determined concentration value associated with a set of depth values, for example, C2= or CT3. However, not including too many traces on the visual mud gas log may bring visual clarity that improves overall safety.

The mud gas log 256 shows traces 280 of mud gas data 258 on a logarithmic basis 260 versus a linear basis 262 for the depth values of the given depth interval. Although a mud gas log may also display such traces on a linear basis, logarithmic basis can also be used. Using logarithmic basis can provide an operator with a more refined impression of the happenings within the wellbore. A sudden increase or decrease in detected mud gas values on the logarithmic scale would represent a factor of 10× increase/decrease in gas concentrations. Such a dramatic change, which may be very difficult to see on a linear scale, may indicate a "kick" from a hydrocarbon-bearing formation or a lost mud situation in a formation. A logarithmic scale event represents a change in order of magnitude—a significant event—from typically minimal concentrations of an alkane gases in the circulating wellbore mud. Second, the use of the logarithmic scale dampens what is considered normal process variability of detected and determined mud gas values during formation of the wellbore. Use of the logarithmic scale for mud gas observation permits easier determination of trends and events that require operator or computer intervention versus the linear scale of mud gas values. A linear scale may not permit as easily of recognition of a significant change or a slow-building trend that occur as values of orders of magnitude may swing back-and-forth. Ensuring that a slow-building trend is recognized is important for effective, efficient and safe operations. This is especially true when using a visual logging system to display both current and historical information as traces.

In some embodiments, the determined concentration trace is associated mathematically with one of the two detected concentrations traces. In some such embodiments, the determine concentration trace is the total C2 gas concentration trace and the one of the two detected concentration traces is the ethane concentration trace. One of the issues with using a logarithmic scale system is the minimization of small numbers, especially values are at or near zero. For example, a value change for mud gas log 256 near the value "0 ppm" may barely register. During drilling operations, it may not even be visually observable. Such a change, as previously indicated, is also important when looking at historical records for the potential formation of artifacts. The solution is the plotting of the determined total concentration trend alongside an associated detected concentration trend. By showing and plotting determined total concentration values, such as total C2 gas concentration, with one of the detected values used to determine the total concentration value, such as ethane concentration, an trained operator, a geologist, or a reservoir engineer, can immediately recognize any divergence—two lines separating from one another—as being artifacts, that is ethylene, in the mud gas. Because the determined value is a total of the two detected values and one of the two determined values is traced along with the determined value, the void or space formed in the log between the detected and determined traces must be the value of the untraced concentration. The separation of two traces, which normally should be the same value (when ethylene=0, ethane concentration=total C2 gas concentration), provides visual impact that alerts an observer versus a dedicated trace line that may never visually be perceived as changing.

In some embodiments, the area between a first trace and a second trace in a visually displayed mud gas log for a given interval is visually highlighted in a color or pattern. In some embodiments, the well control system may perform a determination using an algorithm to determine the area between two concentration traces based upon a set of instructions, and then visually highlight the area as such an output on a visual mud gas log. The difference between the a detected concentration value and a determined concentration value may warrant additional indicators to signal an event occurrence, especially for operators. For example, mud gas log 256 as shown in FIG. 2 has been "enhanced" from a typical mud gas log that reports a set of numbers or trend lines versus depth. Mud gas log 256 shows two particular areas between two sets of trend lines that have been highlighted with a color or pattern on the plotted mud gas log.

In an embodiment, the area between the detected methane concentration trace and the determined total C2 gas concentration trace for a given interval is highlighted in a color or pattern. For the example mud gas log 256, the visual area between the methane trace 282 and the C2T trace 286 is referred to as "first area difference" (290). The first area difference 290 is an aggregation of a plurality of determined first differences for a series of depths, that is, the calculated difference between the detected concentration of methane and the determined concentration of total C2 gas for a given depth interval. First area difference 290 is shaded a first color or pattern, for example, a solid pink or a first diagonal pattern.

In an embodiment, the area between the detected ethane concentration trace and the determined total C2 gas concentration trace for a given interval is highlighted in a color or pattern. For the example mud gas log 256, the visual area between, the visual area between the ethane trace 284 and the C2T trace 286 is referred to as "second area difference" (292). The second area difference 292 is an aggregation of a plurality of determined second differences for a series of depths, that is, the calculated difference between the detected concentration of ethane and the determined concentration of total C2 gas for a given depth interval. Second area difference 292 is shaded a second color or pattern, such as a solid orange or a second diagonal pattern.

In some other embodiments, one or more areas between two sets of traces may be highlighted. Mud gas log may have as many areas highlighted as one may choose. However, the reasoning behind displaying the shading of, for example, first and second areas differences 290, 292 on mud gas log 256, is similar to the reasoning displaying the determined and associated detected concentration trend lines—to bring attention to an observer potential changes and trends that are determined beforehand as being significant and worthy of attention and action. In some instances, the generation of gas artifacts during drilling operations is considered such a potential change. Visually highlighting increases or decreases in relative differences between certain variables may bring visual clarity that improves overall safety.

In some embodiments, a determined event classification is visually displayed in a visually displayed mud gas log. In some embodiments of the method, the well control system may perform a determination using an algorithm to classify a set of detected and determined concentration values based upon a set of instructions, and then visually display an output of the determination on a visual mud gas log. In an instance, the determination by the well control system may indicate that any one of a number of event classifications may fit within a set of instructions and an algorithm for applying the instructions, and then may print or visually mark such. For example, during regular operations the mark "No Event" may be indicted on a mud gas log periodically, such as a word alongside the traces. As well, under different circumstances, other marks such as "Minor Event", "Major Event", and "Severe Event", may be indicated on the mud gas log when appropriate given the detected and determined gas concentration values.

To provide an example of the usefulness of the visual indicators to the modified mud gas log, the mud gas log 256 of FIG. 2 has been segmented into at least four sections (using dashed lines) for discussion purposes: First Event 210, Second Event 212, Third Event 214, and Fourth Event 216. It is noted that two different portions of mud gas log 256 are labeled First Event 210—both are equivalent for discussion purposes. Discussion of the four Events 210, 212, 214, 216 will highlight the number of useful visual identifiers previously described used in combination; however, each may be used on their own or together as seen fit.

First Event 210 more or less represents what would be expected in a mud gas log 256 during normal or typical drilling operations—a period of non-artifact generation. As seen in FIG. 2, the ethane trace 284 completely overlays the C2T trace 286; the detected concentration of ethane 274 and the determined concentration of total C2 gas 272 are the same at the respective depth interval of First Event. No gas artifacts—ethylene—appear to be present as the two traces do not deviate. As would be expected due to their relative concentrations that occur naturally, detected concentration of methane 276 is greater than detected concentration of ethane 274 for all depths of First Event. Because of the logarithmic scale, the visual appearance of first area difference 290 (difference between the logarithmic values of the methane trace 282 and the C2T trace 286) is thin and fairly uniform in width. This is despite the process system variability as the values of detected concentration of methane 276 and determined concentration of total C2 gas 272 fluctuate with the change in depth. First area difference 290 is shaded with a first diagonal pattern so it stands out against the background of the mud gas log 256. The tag "NO EVENT" 251 may be applied, such as in red capitalized text, to the section of the mud gas log 256 periodically to memorialize the determination of the well control system 188.

In instances where it does not appear that gas artifacts are being created during the drilling operation, an operator may examine the rate of penetration (ROP) and consider either maintaining the ROP (if the rate of drilling is considered satisfactory) or increasing the ROP. After an increase to ROP, an operator should consider giving the drilling system a period to achieve a new "steady state" condition, including the composition and concentration of mud gases, to determine if the new condition is still safe, effective and efficient.

In the view of a geologist or reservoir engineer examining a mud gas log, the detection of alkanes (that is, methane, ethane, propane, butanes, pentanes) without the detection of artifacts (that is, ethylene, propylene) is a strong indication that a hydrocarbon-bearing formation has been penetrated proximate to the driller's depth. With such an indication, further testing may be warranted to examine the zone where the mud gases were detected.

Second Event 212 shows an area of the mud gas log 256 where there appears to be indications of a "minor" (relative to other examples) thermal cracking of formation gases. Gas artifacts are present and displayed on mud gas log 256 even though there is no ethylene concentration trace shown. The detected concentration of ethane 274 is less than the determined concentration of total C2 gas 272. During the period of Second Event 212, this creates an ethane trace 284 that is less than the C2T trace 286 on the logarithmic scale. This divergence of the traces 284, 286 indicates the presence of ethylene in the mud gas. Because of the logarithmic scale, the visual appearance of first area difference 290, which was previously described, is greater than the second area difference 292, which is the area between the logarithmic values of the C2T trace 286 and the ethane trace 284. As first area difference 290 and second area difference 292 have different colors or patterns, if the divergence of the traces 284, 286 did not merit notice then the appearance of second area difference 292 should be visually apparent to a viewer of the mud gas log 256. The tag "MINOR EVENT" 253 may be applied to the section of the mud gas log 256 to memorialize the determination.

In instances where it appears that a minor artifact event is occurring, that is, where the first area difference is greater than the second area of difference and that ethylene is detected, an operator may examine the rate of penetration (ROP) and consider reducing the ROP. After a decrease to ROP, just as before, an operator should consider giving the drilling system a period to achieve a new "steady state" condition, to determine if the artifact gases are no longer detectable.

In the view of a geologist or reservoir engineer examining a mud gas log, the detection of some artifacts with a significant amount of alkanes (that is, methane, ethane, propane, butanes, pentanes) without the detection of artifacts (that is, ethylene, propylene) is a strong indication that a hydrocarbon-bearing formation has been penetrated proximate to the driller's depth. With such an indication, further testing may be warranted to examine the zone where the mud gases were detected.

Third Event 214 shows an area of the mud gas log 256 where there appears to be indications of "major" thermal cracking of formation gases. As with Second Event 212, gas artifacts are shown as detected because ethane trace 284 that is less than the C2T trace 286, indicating an increased concentration of ethylene present in the mud gas. Because of the logarithmic scale, the visual appearance of first area difference 290 is equal to or less than second area difference 292. Third Event is a major artifact generation event. The tag "MAJOR EVENT" 255 may be applied to the section of the mud gas log 256 to memorialize the determination.

In instances where it appears that a major artifact event is occurring, that is, where the first area difference is less than or equal to than the second area of difference and that ethylene is detected, an operator may examine the rate of penetration (ROP) and the weight-on-bit (WOB), and consider reducing one or both values in an attempt to mitigate the event. The operator may also begin reviewing other information to determine if there is an issue with the drill bit, such as excessive wear or a long duration of use. After a decrease to one or more of the drilling parameters, the operator should consider giving the drilling system a period to achieve a new "steady state" condition, to determine if the artifact gases decrease or are no longer detectable. Drilling operations may begin to plan to have downtime to change the drill bit due to signs of increased surface friction due to wear.

In the view of a geologist or reservoir engineer examining a mud gas log, the detection of a significant portion of the light gases in the mud gas log comprise artifacts suggests that further sampling or testing may be required to determine if the area at the driller's depth is hydrocarbon bearing or not. In some instances, the geologist or reservoir engineer may suggest a continuation of drilling without further testing depending on the absolute values of the detected mud gases and artifacts, such as when there are high artifact values but low overall mud gases.

Fourth Event 216 shows an area of the mud gas log 256 where there appears to be indications of "extreme" thermal cracking. As with the Second Event 212 and Third Events 214, gas artifacts are apparent due to the divergence of the ethane trace 284 from C2T trace 286. As well, the determined concentration of total C2 gas 272 is greater than the detected concentration of methane 276, which during the period of Fourth Event creates a methane trace 282 that is less than the C2T trace 286 on the logarithmic scale. Because of the logarithmic scale, the visual appearance of the second area difference 292 is present; the first area difference 290 is not present in Fourth Event 216. Because first area difference 290 and second area difference 292 have different colors or shading patterns, the omission of the color or pattern associated with the first area difference 290 from the mud gas log 256 would indicate to a viewer that the conditions for severe levels of artifact gas generation had been satisfied. The tag "SEVERE EVENT" 255 may be applied to the section of the mud gas log 256 to memorialize the determination.

In instances where it appears that a severe artifact event is occurring, that is, where the second area difference dominates the visual mud gas log and that ethylene is detected, an operator may examine the rate of penetration (ROP) and the weight-on-bit (WOB), and consider reducing one or both values in an attempt to mitigate the event. As well, the operator may consider halting drilling operations completely to permit the bit and formation surface to cool under mud fluid flow circulation. After the cessation or decrease to one or more of the drilling parameters, the operator should consider giving the drilling system a period to achieve a new "steady state" condition, to determine if the artifact gases decrease or are no longer detectable. Drilling operations, the rig foreman, and the company man may initiate downtime to trip the downhole assembly (DHA) to the surface to change the drill bit and avoid creating "junk" in the hole.

In the view of a geologist or reservoir engineer examining a mud gas log, the fact that almost all of the light gases detected in the mud gas are methane and cracked gases strongly suggests that the area is not appropriate for production. Unless there is some other indication that the zone has potential hydrocarbons, it may be suggested that drilling past the area where the severe artifacts are detected should proceed once normal drilling operations resume.

It is envisioned that other forms of temporary or permanent designation of event classification, such as text, symbols, graphics, alarms, and lights, displayed visually or permanently on a record, may be used to indicate a set of conditional criteria being met.

Figure 3:
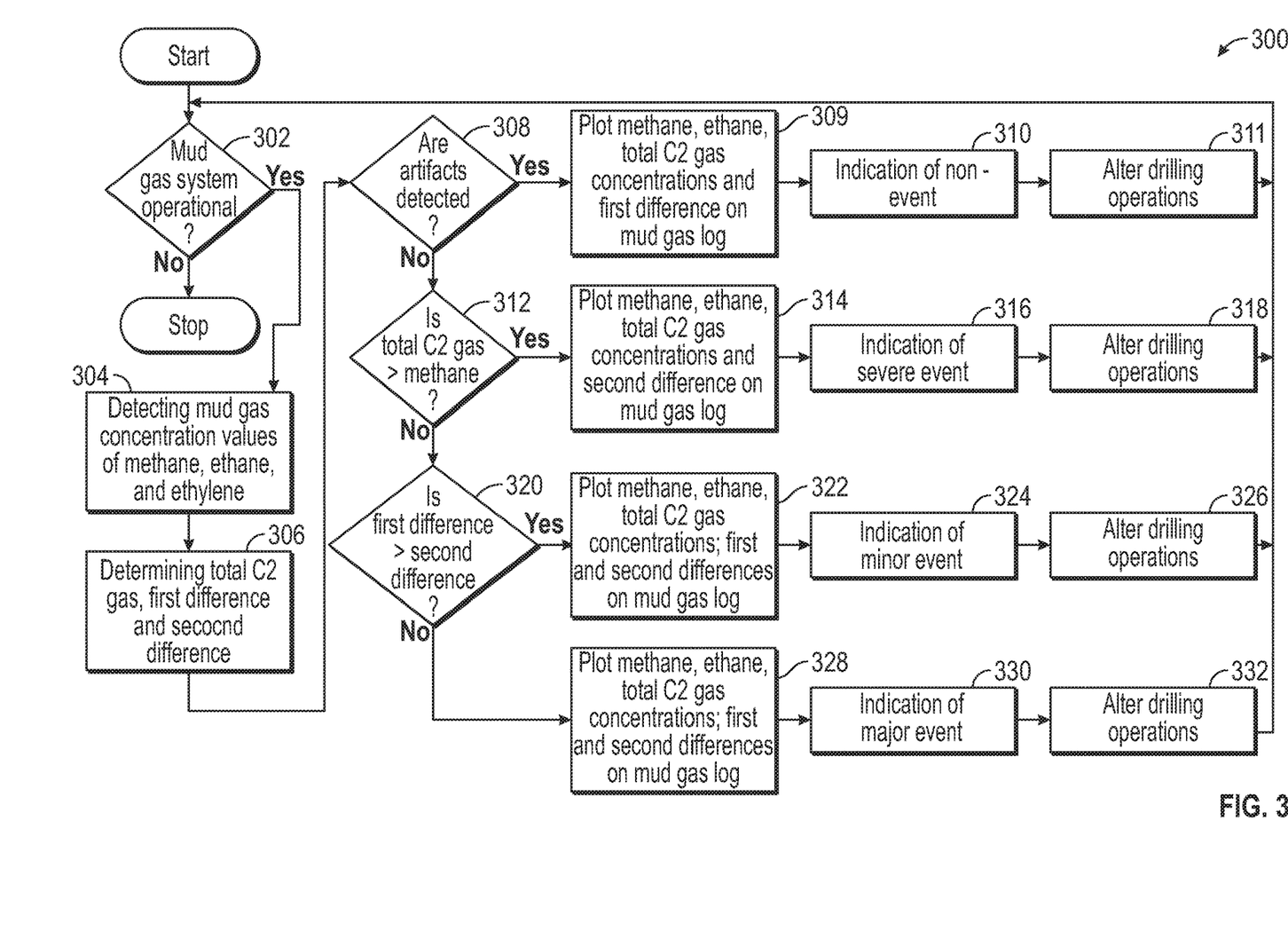
FIG. 3 is a flowchart that illustrates a method of determining the level of an artifact generation event in accordance with one or more embodiments.

FIG. 3 is a flowchart that illustrates a embodiment method 300 of determining the level of an artifact generation event and, optionally, actions to take in accordance with such determination. In the context of the well system, the operational aspects of method 300 may be performed, for example, by the well control system, an operator of the well system, or a combination of both. Embodiment methods may differentiate some or all of a "non-event", a "minor" artifact generation event, a "major" artifact generation event, and a "severe" artifact generation event, some of which has been previously described.

Referring to FIG. 3, in some embodiments, the method 300 may include determining the operational status of the mud system (block 302). For example, obtaining information on the status of the mud circulation system may include processes where the well control system obtains information from the mud circulation system, including the circulation status and parameter values of drilling mud, the status of the total hydrocarbon detector, the high-resolution gas chromatograph, operation of the mud receiving tank, and other measurable, determinable, and detectable variables of the mud circulation system. If the well control system determines that the mud circulation system is satisfactorily operational to the pre-determined instructions required, the method 300 proceeds; otherwise, the method 300 stops.

In some embodiments of the method, the method 300 may include detecting the gas concentration value of the concentration of methane, the concentration of ethane, and the concentration of ethylene at a given depth (block 304). In some instances, the total hydrocarbon detector can detect some or all of the gas concentrations. In some other instances, the gas chromatograph can detect some or all of the gas concentrations. In some other instances, both the total hydrocarbon detector and the gas chromatograph together are used by the mud circulation system, the mud logging system, or the well control system to acquire the detected gas values. Other gas concentration values for other embodiment methods, such as propane and propylene, may be detected by mud logging system 188 and passed to well control system for use. After having passed such concentration values to well controls system, the method moves to block 306.

To help demonstrate the embodiment method 300, several values of concentrations will be provided as a prophetic example. For this example, at a given depth the mud gas log indicates that the detected concentration of methane is about 600 ppm; the detected concentration of ethane is about 150 ppm; and the detected concentration of ethylene is about 300 ppm.

In block 306, several determinations are made by the well control system based upon the detected concentrations of several mud gases. In an embodiment, several determinations are made from the detected concentrations of gases for assessing the degree of artifact gases present in the drilling fluid. In some embodiments, the total C2 gas concentration is determined by summation of the detected concentration of ethylene and the detected concentration of ethane. Total C2 gas concentration has been previously discussed and described in relation to the detected concentrations of ethane and methane. Several other determinations may be made in block 306. In some embodiments, the logarithmic value of the detected concentration of methane is determined. In some embodiments, the logarithmic value of the detected concentration of ethane is determined. In some embodiments, the logarithmic value of the determined total C2 gas concentration is determined. In some embodiments, the difference between the logarithmic value of the detected concentration of methane and the logarithmic value of the determined total C2 gas concentration is determined. The difference between these two values represents the size of the first area difference value displayed on the mud gas log. In some embodiments, the difference between the logarithmic value of the determined total C2 gas concentration and the logarithmic value of the detected concentration of ethane is determined. The difference between these two values represents the size of the second area difference value displayed on the mud gas log. Other determinations depending on the detected concentrations of mud gas and the visual presentations being made in the mud gas log are possible and are envisioned. After these determinations, in some embodiments the method steps to block 308.

In a continuation of the embodiment method 300 with the example detected gas concentration values, the determination of the summation of the detected concentration of ethylene and the detected concentration of ethane is 500 ppm (350+150), which is the value of the determined concentration of total C2 gas. The determination of the log value of the detected concentration of methane is about 2.78. The determination of the logarithmic value of the detected concentration of ethane is about 2.18. The determination of the logarithmic value of the determined concentration of total C2 gas is about 2.70. The determination of the first area difference is 2.78−2.70=0.08. The determination of the second area difference is 2.70−2.18=0.52.

In block 308, embodiment methods include determining if artifact gases are detected. If the method 300 determines that the detected concentration of ethylene is greater than zero, then there are artifact gases in the drilling mud, and the method steps to block 312 to continue. The method 300 then steps to block 312. If the method 300 determines that the concentration of ethylene is zero at a given depth, then the method steps to block 309.

In block 309, the detected concentration of methane, the detected concentration of ethane, the determined concentration of total C2 gas and the determined first area difference are plotted and highlighted, respectively, on a mud gas log at the given depth. Embodiment method 300 then may step to block 310.

Optionally, the method 300 at block 310 may provide an indication of the determination of the non-event. In some embodiments, the method may direct the a control system, such as well control system, to send a signal to an external device or I/O device, such as control terminal, to provide a visual or audio message. In some other embodiments, the method may place an indicator, tag or symbol on a mud gas log, such as "NO EVENT", next to the plotted detected and determined concentration traces to memorialize the determination at the given depth. Embodiment method 300 then may step to block 311.

Optionally, in block 311, the method 300, using an algorithm and pre-determined instructions held in memory of the well control system, may alter the operation of a drilling system in response to the determination of the non-event. For example, the rate of penetration (ROP) may be increased by a fixed percentage compared to the current ROP or by an fixed amount of ROP.

Optionally, a delay timer may be activated in the well control system that does not permit the well control system to alter the operation of the drilling system for a set amount of time, for example, 15 seconds, to permit the drilling system and the wellbore conditions to change come to a new steady state condition before re-evaluation by method 300.

Optionally, an operator may take some or all of any of the previously described actions in light of the well control system indicating through the signal to the external device or I/O device indicating that no event has been determined.

After block 311, method 300 steps to the beginning to run through the method 300 again.

Continuing with the example, the detected concentration of ethylene is more than 0 (350 ppm). An artifact event is occurring at the given depth; therefore, the method steps to block 312 to continue method 300.

In block 312, embodiment methods include determining if the conditions for a severe artifact event are satisfied. If the method 300 determines that the determined concentration of total C2 gas is greater than the detected concentration of methane, then a severe artifact event is occurring at the given depth. The method then steps to block 314. If the method 300 determines that the determined concentration of total C2 gas is equal to or less than the detected concentration of methane, then a non-severe artifact event is occurring at the given depth. The method then steps to block 320.

If it is determined that a severe artifact event is occurring, then in block 314 the detected concentration of methane, the detected concentration of ethane, the determined concentration of total C2 gas and the determined second area difference are plotted and highlighted, respectively, on a mud gas log at the given depth. Embodiment method 300 then steps to block 316.

In block 316, the method 300 may provide an indication of the determination of the severe artifact event. In some embodiments, the method may direct the a control system, such as well control system, to send an alert signal to an external device or I/O device, such as control terminal, to provide a visual or audio alert corresponding to the event. For example, an indicator may be shown on the visual display for the operator, such as "HALT DRILLING" or "POTENTIAL DRILL BIT DAMAGE—INVESTIGATE". In some other embodiments, the method may place an indicator, tag or symbol on a mud gas log, such as "SEVERE EVENT", next to the plotted detected and determined concentration traces to memorialize the determination of the artifact event at the given depth. Embodiment method 300 may then step to block 318.

Optionally, in block 318, the method 300, using an algorithm and pre-determined instructions held in memory of the well control system, may modify the operation of a drilling system in response to the determination of a severe artifact event. For example, the rate of penetration (ROP) may be decreased by a fixed percentage compared to the current ROP or by an fixed amount of ROP. In another instance, the weight-on-bit (WOB) may be decreased by a fixed percentage compared to the current WOB or by an fixed amount of WOB. In some other instances, the revolutions per minute (RPM) of the drill bit or the drill string, depending on the configuration of the drilling system, may be decreased by a fixed percentage compared to the current RPM or by a fixed amount of RPM.

Optionally, after the modification to the drilling system, a delay timer may be activated as previously described.

Optionally, an operator may take some or all of any of the previously described actions.

After block 318, method 300 steps to the beginning to run through the method 300 again.

Continuing with the example, the determined concentration of total C2 gas (500 ppm) is equal to or less than the detected concentration of methane (600 ppm). A non-severe artifact event is occurring at the given depth; therefore, the method steps to block 320 to continue method 300.

In block 320, embodiment methods include determining if the conditions for a minor artifact event are satisfied. If the method 300 determines that the determined first area value is greater than the second area value, both as previously determined in block 306, then the artifact generation event is determined to be a minor event occurring at the given depth. The method then steps to block 322. If the method 300 determines that the determined first area value is less than or equal to the second area value, then the artifact generation event is determined to be a major event occurring at the given depth. The method then steps to block 328.

If it is determined that a minor artifact event is occurring, then in block 322 the detected concentration of methane, the detected concentration of ethane, the determined concentration of total C2 gas, the determined first area difference and the determined second area difference are plotted and highlighted, respectively, on a mud gas log at the given depth. Embodiment method 300 then steps to block 324.

In block 324, the method 300 may provide an indication of the determination of the minor artifact event. In some embodiments, the method may direct the a control system, such as well control system, to send an alert signal to an external device or I/O device, such as control terminal, to provide a visual or audio alert corresponding to the event. In some other embodiments, the method may place an indicator, tag or symbol on a mud gas log, such as "MINOR EVENT", next to the plotted detected and determined concentration traces to memorialize the determination of the artifact event at the given depth. Embodiment method 300 may then step to block 326.

Optionally, in block 326, the method 300, using an algorithm and pre-determined instructions held in memory of the well control system, may modify the operation of a drilling system in response to the determination of a minor artifact event. For example, the rate of penetration (ROP) may be decreased by a fixed percentage compared to the current ROP or by an fixed amount of ROP.

Optionally, after the modification to the drilling system, a delay timer may be activated as previously described.

Optionally, an operator may take some or all of any of the previously described actions.

After block 326, method 300 steps to the beginning to run through the method 300 again.

Continuing with the example, the determined first area difference (0.08) is less than the second area difference (0.52). A minor artifact event is not occurring; rather, a major artifact event is occurring at the given depth. Therefore, the method steps to block 328.

If it is determined that a major artifact event is occurring, then in block 328 the detected concentration of methane, the detected concentration of ethane, the determined concentration of total C2 gas, the determined first area difference and the determined second area difference are plotted and highlighted, respectively, on a mud gas log at the given depth. Embodiment method 300 then steps to block 330.

In block 330, the method 300 may provide an indication of the determination of the major artifact event. In some embodiments, the method may direct the a control system, such as well control system, to send an alert signal to an external device or I/O device, such as control terminal, to provide a visual or audio alert corresponding to the event. For example, an indicator may be shown on the visual display for the operator, such as "REDUCE ROP OR WOB" or "WARNING—POTENTIAL DRILL BIT DAMAGE". In some other embodiments, the method may place an indicator, tag or symbol on a mud gas log, such as "MAJOR EVENT", next to the plotted detected and determined concentration traces to memorialize the determination of the artifact event at the given depth. Embodiment method 300 may then step to block 332.

Optionally, in block 332, the method 300, using an algorithm and pre-determined instructions held in memory of the well control system, may modify the operation of a drilling system in response to the determination of a major artifact event. In some instances, the rate of penetration (ROP) may be decreased by a fixed percentage compared to the current ROP or by an fixed amount of ROP. In another instance, the weight-on-bit (WOB) may be decreased by a fixed percentage compared to the current WOB or by an fixed amount of WOB. In some other instances, the revolutions per minute (RPM) of the drill bit or the drill string, depending on the configuration of the drilling system, may be decreased by a fixed percentage compared to the current RPM or by a fixed amount of RPM.

Optionally, after the modification to the drilling system, a delay timer may be activated as previously described.

Optionally, an operator may take some or all of any of the previously described actions.

After block 332, method 300 steps to the beginning to run through the method 300 again.

The method 300 may continue to loop, detect gas concentration values, determine total gas concentration values, determine the logarithmic values of gas concentrations, provide alert signals, visual indicators, and memorialize the mud gas data and event determinations in the mud gas log, until the mud circulation systems until halted by manual or automated command or until the mud circulation system is no longer operating (block 302). Operation, control and performance of portions of or entire steps of a process or method can occur through human interaction, pre-programmed computer control and response systems, or combinations thereof.

Figure 4:
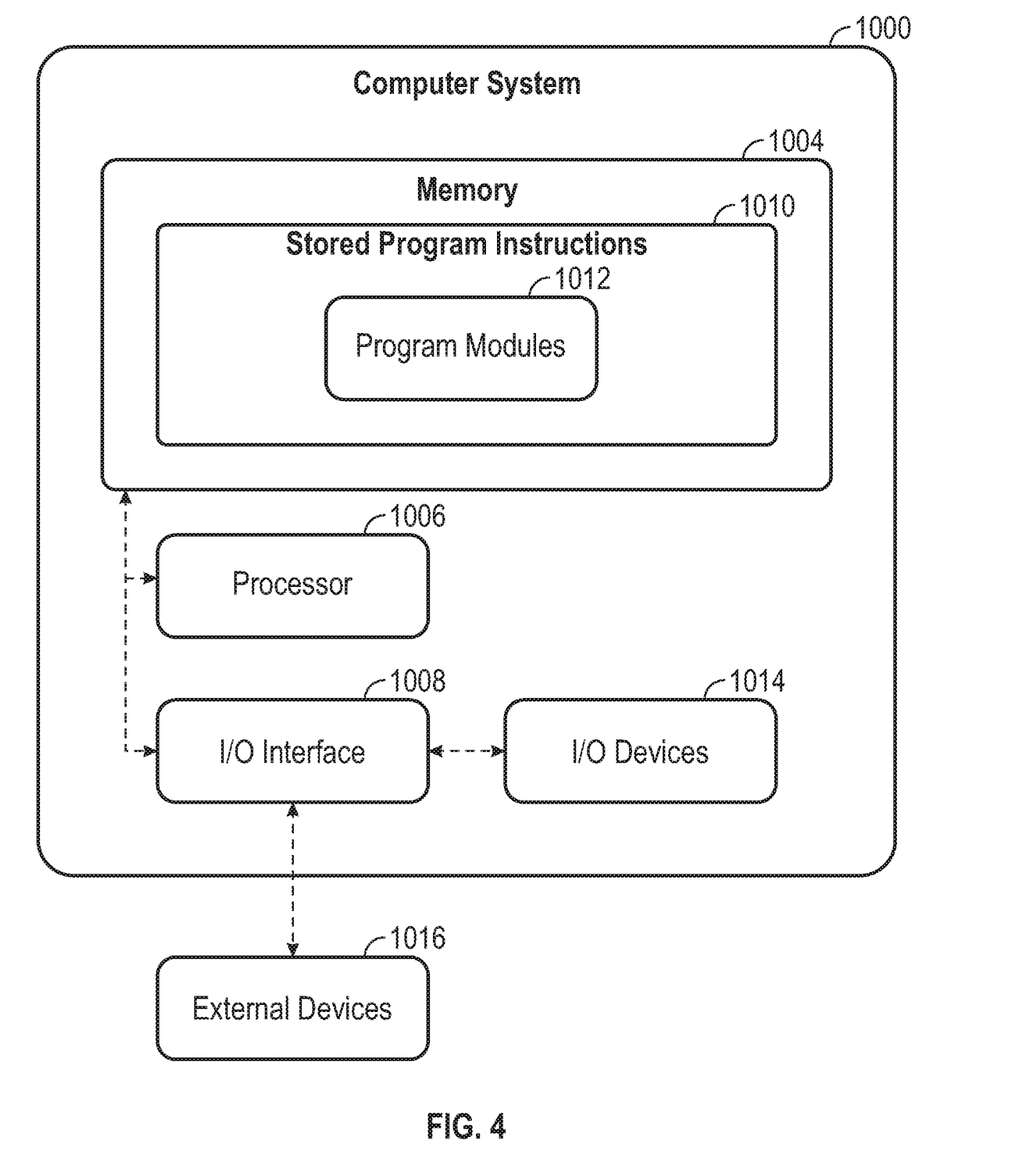
FIG. 4 is a diagram that illustrates an example computer system (or "system") in accordance with one or more embodiments.

FIG. 4 is a diagram that illustrates an example computer system (or "system") 1000 in accordance with one or more embodiments. In some embodiments, the system 1000 is a programmable logic controller (PLC). The system 1000 may include a memory 1004, a processor 1006 and an input/output (I/O) interface 1008. The memory 1004 may include non-volatile memory (for example, flash memory, read-only memory (ROM), programmable read-only memory (PROM), erasable programmable read-only memory (EPROM), electrically erasable programmable read-only memory (EEPROM)), volatile memory (for example, random access memory (RAM), static random access memory (SRAM), synchronous dynamic RAM (SDRAM)), or bulk storage memory (for example, CD-ROM or DVD-ROM, hard drives). The memory 1004 may include a non-transitory computer-readable storage medium having stored program instructions 1010. The program instructions 1010 may include program modules 1012 that are executable by a computer processor (for example, the processor 1006) to cause the functional operations described, such as those described with regard to the well control system 122 (or another operator of the well system 106) or the method 300.

The processor 1006 may be any suitable processor capable of executing program instructions. The processor 1006 may include a central processing unit (CPU) that carries out program instructions (for example, the program instructions of the program modules 1012) to perform the arithmetical, logical, or input/output operations described. The processor 1006 may include one or more processors. The I/O interface 1008 may provide an interface for communication with one or more I/O devices 1014, such as a joystick, a computer mouse, a keyboard, or a display screen (for example, an electronic display for displaying a graphical user interface (GUI)). The I/O devices 1014 may include one or more of the user input devices. The I/O devices 1014 may be connected to the I/O interface 1008 by way of a wired connection (for example, an Industrial Ethernet connection) or a wireless connection (for example, a Wi-Fi connection). The I/O interface 1008 may provide an interface for communication with one or more external devices 1016. In some embodiments, the I/O interface 1008 includes one or both of an antenna and a transceiver. In some embodiments, the external devices 1016 include the drilling system 130, such as control terminal 170 of FIG. 1.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A method comprising:
   collecting a sample of a mud gas from a drilling fluid used during a drilling operation to form a wellbore;
   associating the collected mud gas sample with a depth of the wellbore during the drilling operation;
   detecting the concentration of ethane, the concentration of ethylene, and the concentration of methane in the drilling fluid at the depth;
   determining the concentration of total C2 gases in the drilling fluid at the depth;
   determining a first difference between the logarithmic value of the detected concentration of methane and the logarithmic value of the determined concentration of total C2 gases at the depth;
   determining a second difference between the logarithmic value of the determined concentration of total C2 gases and the logarithmic value of the detected concentration of ethane at the depth;
   determining a degree of artifact gases present in the drilling fluid at the depth based upon the detected concentration of methane and ethylene, and the determined concentration of total C2 gases, the first difference and the second difference; and modifying a visually displayed mud drilling log to reflect the determined degree of artifact gases present in the drilling fluid at the depth.

2. The method of claim 1 where determining the degree of artifact gases present in the drilling fluid at the depth includes determining whether the detected value of the concentration of ethylene in the mud gas is greater than 0.

3. The method of claim 1 where determining the degree of artifact gases present in the drilling fluid at the depth includes determining whether the determined value of the concentration of total C2 gases is greater than the detected value of the concentration of methane in the mud gas.

4. The method of claim 1 where determining the degree of artifact gases present in the drilling fluid at the depth includes determining whether a first difference is greater than a second difference.

5. The method of claim 1 where determining the degree of artifact gases present in the drilling fluid at the depth includes determining whether a first difference is equal to or less than a second difference at the depth.

6. The method of claim 1 further comprising displaying an alert on a visual display associated with the determined degree of artifact gases present in the drilling fluid at the depth.

7. The method of claim 1 further comprising modifying the rotation per minute (RPM) of the drill bit or the drill string, as applicable, used in the drilling operation in response to the determined degree of artifact gases present in the drilling fluid at the depth.

8. The method of claim 1 further comprising modifying the weight-on-bit (WOB) used in the drilling operation in response to the determined degree of artifact gases present in the drilling fluid at the depth.

9. The method of claim 1 further comprising modifying the rate of penetration (ROP) used in the drilling operation in response to the determined degree of artifact gases present in the drilling fluid at the depth.

10. The method of claim 9 where the ROP is increased in response to the determined degree of artifact gases.

11. The method of claim 9 where the ROP is decreased by a fixed percentage of the ROP used in the drilling operation.

12. The method of claim 1 where a first detected concentration trace, a second detected concentration trace, and a determined concentration trace are visually displayed on the mud gas log for a given depth interval.

13. The method of claim 12 where the first detected concentration trace is the concentration of methane, the second detected concentration trace is the concentration of ethane, and the determined concentration trace is the concentration of total C2 gases.

14. The method of claim 13 where the area between the first detected concentration trace and the determined concentration trace is indicated by a first color or pattern.

15. The method of claim 13 where the area between the determined concentration trace and the second detected concentration trace is indicated by a second color or pattern.

* * * * *